(12) United States Patent
Larsen

(10) Patent No.: US 6,450,941 B1
(45) Date of Patent: *Sep. 17, 2002

(54) DEVICE FOR THE STIMULATION OF BODY CELLS THROUGH ELECTROMAGNETIC RADIATION

(76) Inventor: Eric Larsen, Box 400/Hochstr. 309, 8201 Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/530,338
(22) PCT Filed: Jan. 18, 1995
(86) PCT No.: PCT/CH95/00012
§ 371 (c)(1),
(2), (4) Date: Jan. 31, 1997
(87) PCT Pub. No.: WO95/19808
PCT Pub. Date: Jul. 27, 1995

(30) Foreign Application Priority Data

Jan. 21, 1994 (CH) ............................................. 183/94

(51) Int. Cl.[7] ................................................. A61N 1/00
(52) U.S. Cl. ......................................... 600/14; 600/15
(58) Field of Search ..................................... 600/9–15

(56) References Cited

FOREIGN PATENT DOCUMENTS

| DE | 3404214 | * | 8/1985 |
| GB | 2262043 | * | 6/1993 |
| WO | 9309847 | * | 5/1993 |

* cited by examiner

Primary Examiner—John P. Lacyk
(74) Attorney, Agent, or Firm—Cohen, Pontani, Lieberman & Pavane

(57) ABSTRACT

The invented device for hair-care consists of an applicator (1), which is equipped with at least one print-board (6,7), upon which semiconductor-diodes (LED) or laser-diodes (8) are placed. The semiconductor-diodes (LED) and the laser-diodes radiate light with a wavelength between 350 and 1200 nm. Further, the applicator (1) contains one or more plain transmitter-coils (transducers) (3) for the emission of pulse-shaped electromagnetic radiation. It can be equipped with an IR-heating element and a ventilator to produce a warm air stream. The applicator (1) can be formed as a hood (2) or designed as a plainer surface applicator consisting of one or more parts, in the latter case the parts being connected with moveable joints. The applicator can also be designed as a hand applicator. In this case it resembles an ordinary hand-held hair drier, consisting of an almost cylindrical tube with a rectangular handle.

9 Claims, 2 Drawing Sheets

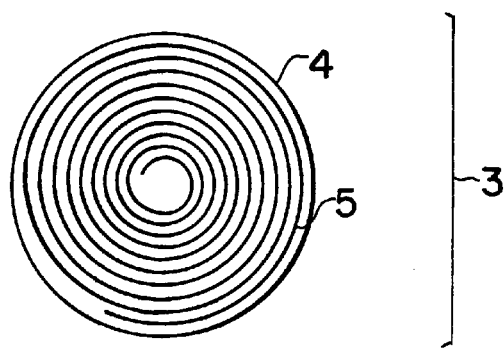
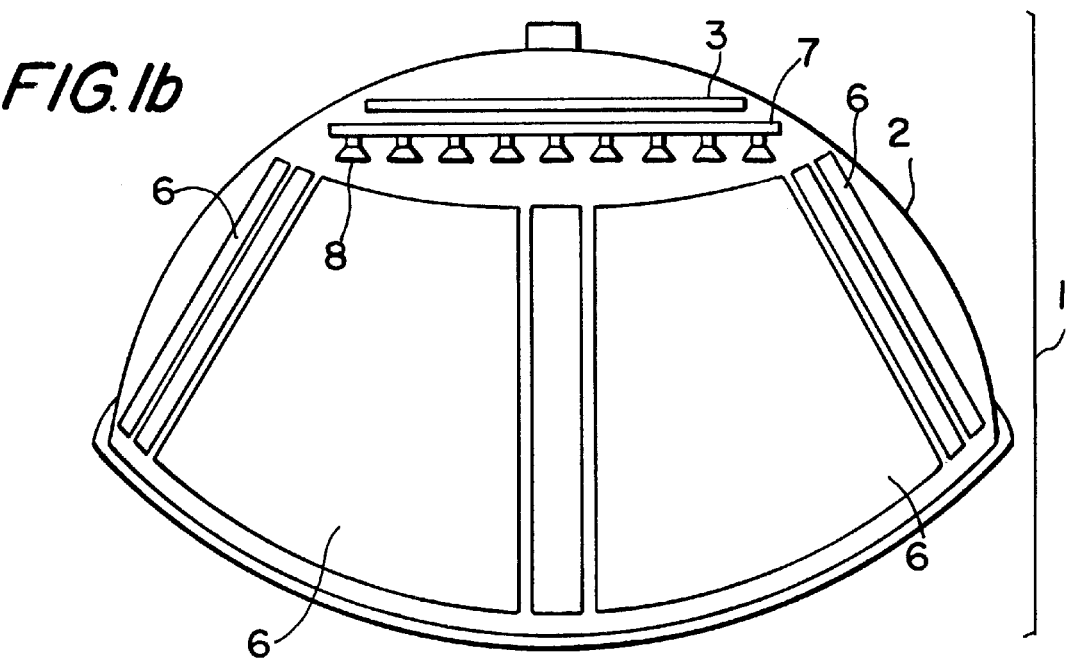
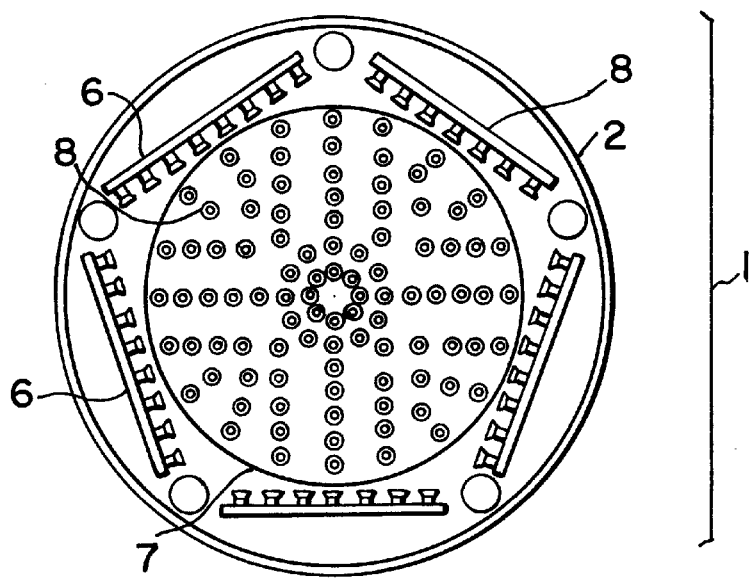

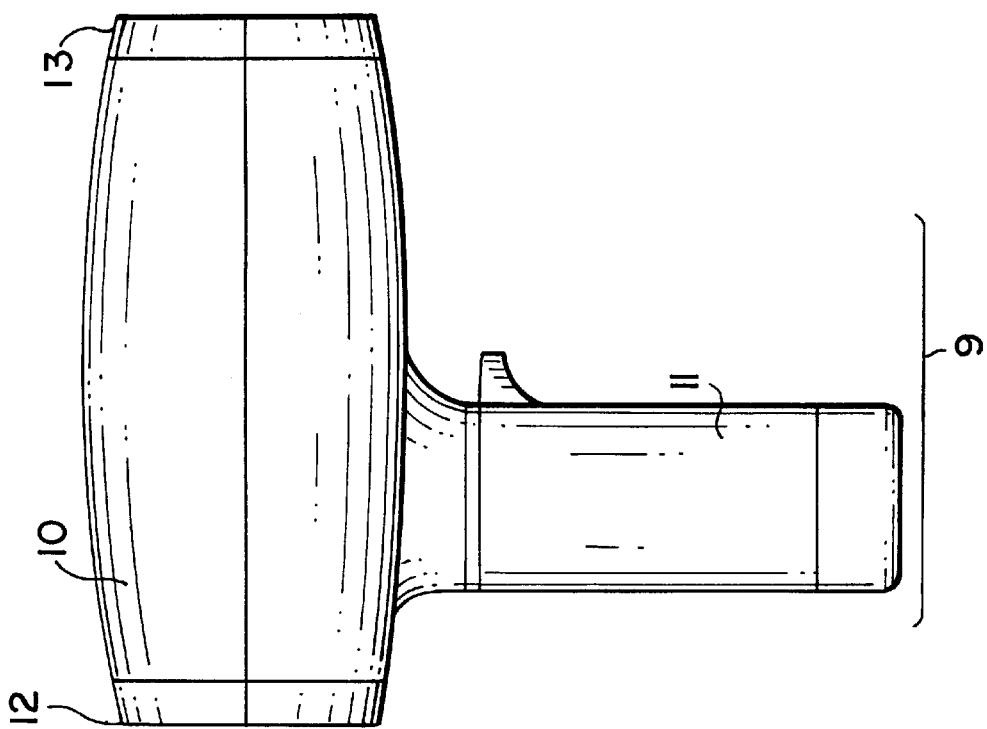

DEVICE FOR THE STIMULATION OF BODY CELLS THROUGH ELECTROMAGNETIC RADIATION

Our affluent society exposes our bodies and our hair to a great many strains. The food we eat contains too high a nitrate content, and the air we breathe is heavily polluted with nitric oxides, sodium oxides, ozone and soot particles. The heavy metals which we absorb through our food and air impair enzyme activity. We are often exposed to stressful situations, which cause a contraction of blood vessels and a decrease in blood circulation. Statistical surveys show that a rising number of persons suffer from allergies, eczema and hair problems. The reasons for this, aside from hereditary factors, can be seen in a combination of the above mentioned influences and the multitude of chemical treatments offered by present-day hair-dressing.

In order to improve hair quality and prevent scalp diseases research was started to develop a combination device which could improve the blood circulation and vitality of the scalp. Medical research has been able to show that ailing body cells can, through irradiation with infrared light, be energized and regenerated. The infrared light has the following effects on body cells:

Within the cells of protozoans, animals and humans can be found polymorphic organeiles approximately o,5–1$\mu$m wide and 1–6$\mu$m long the so called mitochondria. Depending on the kind of cell, the number of mitochondria can vary from just a couple to several hundred thousand pr. cell. The mitochondria are the source of energy for cell respiration. Through cell respiration, the nutrients which reach the mitochondria via the bloodstream are transformed, together with inhaled oxygen, into water, carbon dioxide, alcohol, lactic acid and other waste products—but most importantly into energy and building materials for the body.

Of great importance as a carrier of the produced energy is adenosine triphosphoric acid (ATP), which is synthesized by the mitochondria from adenosine-diphosphoric acid and orthophosphate. Very important for this synthesis are complex biochemical molecules which operate as reaction catalysts (enzymes). It has been medically proved that it is possible to stimulate the ATP production of the mitochondria through optic radiation. Such a stimulation can be effected with a continuous radiation beam and a pulsed beam as long as the wavelength is correct. If the radiation is pulsed the selection of the right frequency is very important. The radiation beam must also have a sufficient penetration depth to enable it to reach the tissue area which is to be stimulated.

Light radiation within the infrared light range (600–1200 nm) has been discovered to be capable of stimulating the mitochondria while at the same time possessing a sufficient penetration depth. In addition to infrared light, blue light within the wavelength range 350–450 nm has shown the ability to improve the vitality of body cells. Light in the blue fight range is able to enhance various intracellular activities, thereby accelerating the regeneration of fatigued or ailing tissue.

Moreover, pulsating electromagnetic fields have shown to exert a positive influence on the bodies of both animals and humans. With the help of pulsating electromagnetic fields it is possible to send protons from electrolytic internal body fluids such as blood or lymph directly and in controlled measures into the surrounding vessels wall and membranes. This is normally not possible, since the lipids in the membranes of the blood vessel walls, which are in contact with the blood, carry a negative charge creating a surface potential which hinders the protons and ions from entering the vessel walls. The pulsating electromagnetic field enables the protons to enter the cell and vessel walls in spite of the barrier. When this occurs, the increased concentration of protons within the cell and vessel walls reverses the polarity of the barrier, thereby hindering the protons and ions from exiting through the cell and vessel walls again.

In turn, this phenomenon causes a beneficial change in the local pH value, especially within the vessel walls. Additionally, prolonged exposure to pulsating electromagnetic fields has other effects, such as the electrical constriction of the membranes and vessel walls, the adjustment of polyvalent ion chains, the tangential displacement of absorbed counter ions, the force effect on dielectric bodies in homogeneous and nonhomogeneous fields, and electro-osmosis.

In the context of hair-care, another important effect of photodynamic energy stimulation and electromagnetic fields can be mentioned.

During the treatment of hair with products such as hair-colour or dye, chemical reactions take place. The energy necessary for the reaction can be provided in the form of electro magnetic radiation and in the form of light within a suitable wavelength range. This causes an acceleration of the chemical reaction. Such an acceleration can also be brought by using heat rays, but with the one important disadvantage that the entire area (Hair and scalp) is unnecessarily warmed. This is avoided when electromagnetic radiation and light are used.

Looking at the current state of technology, devices are available for the photodynamic stimulation of the mitocondria activity by infrared radiation, where the infrared radiation is produced through semiconductor diodes or laser diodes. But these devices cannot be used for hair-care because they lack suitable applicators. Moreover, a combined treatment with both infrared light and pulsating electromagnetic fields is not possible with these devices. Furthermore devices for the application of pulsating electromagnetical fields are also wellknown. But these devices are not suitable for hair-care due to the lack of suitable applicators. The mentioned devices for application of pulsating electromagnetic fields can moreover not be used for combination treatment with infrared light radiation.

It would be advantageous if the device combining infrared light radiation, blue light radiation and electromagnetic fields also could emit a warm air stream. Thereby the device could also dry wet hair during the treatment.

A device able to deliver infrared radiation, light within the blue range, electromagnetic radiation and hot air is not at present available.

Hence, the invention is aimed at creating a device for hair-care which is capable of photodynamic energy stimulation with both infrared and blue light, treatment with pulsating electromagnetic fields and hot air.

The invention is constructed according to the description of patent claim 1.

The invention consists of a suitably designed applicator with at least one print-board on which semiconductor diodes or laser diodes are arranged. The applicator also includes one or more transducers for the emission of pulse-shaped electromagnetic radiation, and a bellows heating element for the generation of a hot air current. The applicator is hood-shaped and has an appearance resembling that of an ordinary hair-drier hood. The applicator can also be made in a hand-held version, and in this case resembles an ordinary hand-held hair-drier, consisting of an almost cylindrical tube with a rectangular handle protruding at the rear.

The applicator can also be constructed as a flat surface-applicator.

The invention is, amongst other things, illustrated in the diagrams, which shows:

FIG. 1a Flat transmitter coil (transducer) viewed from above, with spiral transmitter-winding.

FIG. 1b Applicator hood, side-view.

FIG. 1c Applicator hood, viewed from below.

FIG. 2a Hand applicator, side-view.

FIG. 2b Print-board with semiconductor diodes or laser diodes and openings for hot air, viewed from above.

Applicator 1 is hood-shaped with a circular cross-section (FIG. 1). It can be positioned over the head of the person to be treated in the same way as a drier-hood. For this purpose the applicator is mounted on a stand or a jointed arm (not illustrated). Inside the bowl 2 of the hood, a flat transmitter-coil (transducer) 3 is located at its vertex. The transmitter coil 3 consists of a circular base plate 4 on which a transmitter winding of circular spiral shape is placed on one or both sides.

The transmitter winding of the transmitter coil can be shaped as a quadripole.

The transmitter coil 3 is placed perpendicular to the bowl longitudinal axis. The generator for producing the necessary current pulses is located in a control unit, which also contains the current supply and a control mechanism with keyboard (not illustrated). Supplementary to the transmitter coil 3, several trapezoidal print-boards 6 and a circular print-board 7 are placed in the hood's interior 2. The circular print-board 7 is placed in the upper area of the bowl 2. It is located closely below the transmitter coil 3 and almost parallel with this. The trapezoidal print-boards are placed laterally within the bowl 2, spread at regular intervals around its circumference, and narrowing to the top. FIG. 1 illustrates a version of the hood-applicator 1 with five pieces trapezoidal print-boards 6. The lower edges of the print-boards form a regular pentagon. These print-boards 6, 7, carry semiconductor diodes 8 or laser diodes 8 for the generation of infrared light and light within the blue range. The print-boards 6, 7 are equipped with semiconductor diodes 8 in alternate order.

They are supplied with current pulse frequencies of 200–20000 Hz and current pulse lengths of between 2 and 200 microseconds, preferably 2–20 microseconds and current pulse amplitudes between 15 and 25 Volts. Operating in this manner, utilizing a short current pulse length, thermal build-up is avoided and it is therefore possible to work with a constant effect. When the apparatus is operating in this mode there appears simultaneously at each infrared semiconductor diode 8 light radiation within three separate wavelength ranges, in the ranges 600, 900 and 1200 nm. Through a synchronous stimulation of the semiconductor diodes 8 and the blue light diodes 8—four radiation wavelengths become available for therapeutic use, 400 nm (blue light) and 600, 900 and 1200 nm. In addition to the above semiconductor operating mode, another mode is available—the laser mode. In this mode the print-boards are equipped with laser diodes instead of semiconductor diodes. The laser diodes are supplied with current impulses of a frequency between 200 and 20000 Hz, a current pulse length between 2 and 200 nanoseconds, preferably between 2 and 20 nanoseconds and a current pulse amplitude between 40 and 400 Volts. A monochromatic laser light with a preferable wavelength of about 900 nm is generated and can be used for therapeutic purposes just as well as light of a comparable wavelength generated by semiconductor diodes, under the precondition that the current pulse length for photodynamic stimulation in the—laser mode falls within 2–200 nanoseconds.

The current impulses necessary for the generation of the light are also produced by a generator located in a control unit (not illustrated).

The heating element supplies the hood with hot air for hair-drying via a pipe. The hot air is blown through jets into the inside of the bowl 2, (not illustrated).

A second possible version of the applicator is the hand model 9. At the rear of the almost cylindrical tube is a rectangular handle, the rear edge of which forms a straight line with the rear of the tube 10. At the front 13 of the tube 10 is a circular print-board 14 which is divided into four ring-shaped areas 15, 16, 17, 18, and a circular central area 19. The outermost ring 15 is equipped with semiconductor diodes 8 and/or laser diodes 8. The second outermost ring 16 is divided into four quadrants 19, two of which are equipped with semiconductor diodes and/or laser diodes 8, the other two with air vents 20 for the hot air 20. The quadrants containing diodes 8 and the quadrants containing air-vents 20 are placed alternately. The second innermost ring 17 is equipped and arranged in the same way as the second outermost ring 16, while the innermost ring 18 is identical to the outermost ring. The circular central area 19 is a grid which allows the passage of hot air.

The generator for producing the current pulses with which the semiconductor diodes and/or laser diodes 8 are supplied is located in the tube 10. The tube 10 also contains the ventilator and heating coils for generating the hot air current which is emitted through the front 13 of the tube via the air vents 20 and the grid area 19 on print-board 14. Also located in the tube 10 of the hand applicator 9 is a control unit. The hand applicator 9, like the hood applicator, has two operating modes semiconductor and laser.

The applicator and can also be designed as a flat surface applicator with both semiconductor diodes and/or laser diodes and one or more transmitter coils (transducers). The surface applicator can consist of one or more parts—in the latter case the separate parts being in moveable jointed sections.

The suggested applicators 1 and 9 enable for the first time the use of photodynamic stimulation and electromagnetic field treatment in hair-care.

The infrared photons which penetrate the tissues are absorbed by a light-sensitive enzyme (biocatalyst), within the mitochondria of body cells. In this way the generation of the energy carrier molecule ATP is increased, thus stimulating the vital processes of the scalp. The hair and the scalp are regenerated.

The weak inductive electromagnetic waves activate the circulation by means of microvibration, causing a vasodilatation and restoring the functional ability of contracted or occluded blood vessels. The blood supply of the hair follicles and scalp is improved, and thereby the oxygenation of the cells of the hair scalp. The hair growth period is optimized, and balanced with the ensuing rest period.

The radiation of the semiconductor diodes accelerates chemical processes, resulting in an improved binding of the colour molecules during hair dying or tinting. The hair can now be more easily styled. Combined with the use of a vitamin cure, a conditioner or other hair-care products, the treatment enables better absorption by the hair and the scalp, thereby optimizing the quality and duration of their effects.

The suggested applicators 1 and 9 enable a noiseless treatment without unpleasant heat. They shorten the working time of chemical hair treatments. Treatment of hair with electromagnetic fields and photodynamic energy stimulation gives the hair more shine and has a general balancing effect on hair loss, dandruff, seborrhea, alopaecia areata and other trichoses. It is well known that excessive heat for the drying of wet hair has a desiccative and noxious effect on the hair. The applicators 1 and 9 enable the drying of wet hair through radiation by semiconductor diodes within the wavelength range of 600–1200 nm. A ventilator sends an air flow past the semiconductor diodes towards the treatment area. The air flow is warmed to body temperature (37° Celsius) by a heating element.

The accelerating effect of the semiconductor diode radiation on chemical processes can be used not only for haircare, but also for other purposes, for example the hardening of agglutinate plastics.

INDEX TO NUMBERED PARTLIST

1. Hood shaped applicator
2. Hood shaped bowl
3. Flat transducer
4. Circular base plate
5. Transmitter-windings
6. Trapezoid shaped print-board
7. Circular print-board
8. Semiconductor diodes—respectively laser diodes
9. Hand-applicator
10. Applicator-housing
11. Handle
12. Posterior front of the applicator-housing
13. Anterior front of the applicator-housing
14. Print-board
15. Outermost ringshaped print-board area
16. Second outermost ringshaped print-board area
17. Second innermost ringshaped print-board area
18. Innermost ringshaped print-board area
19. Circular shaped central area
20. Air vent for hot air

What is claimed is:

1. A device for stimulation of body cells, acceleration of chemical processes, and the drying of wet hair comprising:
    an applicator including;
        a plurality of diodes including at least one light emitting diode and at least one laser diode;
        said plurality of diodes comprising:
            diodes for emitting radiation at approximately 600 nm, 900 nm and 1200 nm and a diode for emitting radiation in the range of 350 to 450 nm.
        a coil for producing an electromagnetic field;
        a heating element;
        a fan for producing an air flow; and
        a control and power unit for activating said plurality of diodes, said coil, said heating element and said fan; said control and power unit for activating said plurality of diodes with pulses having an amplitude between 15 and 25 volts, a pulse length between 2 and 200 nanoseconds and a pulse frequency between 1 and 20 KHz.

2. The device according to claim 1, wherein the pulse duration is between 2 and 20 nanoseconds.

3. A device for stimulation of body cells, acceleration of chemical processes, and the drying of wet hair comprising:
    an applicator including;
        a plurality of diodes including at least one light emitting diode and at least and one laser diode;
        said plurality of diodes comprising:
            diodes for emitting radiation at approximately 600 nm, 900 nm and 1200 nm and a diode for emitting radiation in the range of 350 to 450 nm;
        a coil for producing an electromagnetic field;
        a heating element;
        a fan for producing an air flow; and
        a control and power unit for activating said plurality of diodes, said coil, said heating element and said fan; and
        said control and power unit for activating said plurality of diodes with pulses having an amplitude between 40 and 400 volts, a pulse length between 2 and 200 nanoseconds, and a pulse frequency between 0.2 and 20 KHz.

4. The device according to claim 3, wherein the pulse duration is between 2 and 20 nanoseconds.

5. A device for stimulation of body cells, acceleration of chemical processes, and the drying of wet hair, comprising:
    an applicator comprising:
        a plurality of diodes for emitting light;
        a coil for producing an electromagnetic field;
        a heating element;
        a fan for producing an air flow;
        a control and power unit for activating the diodes, coil, heating element, and fan;
        said control and power unit for also activating said coil with base pulses having a frequency between 2 and 500 Hz.;
        ON times of about three-tenths of a period;
        OFF times of about seven-tenths of a period; and
        non-instantaneous rise and fall times.

6. The device according to claim 5, wherein:
    the control and power unit superimposes pulse-bundles on the base pulses;
    wherein the pulse-bundles comprise pulses having a frequency of about 10 kHz.

7. A device for stimulation of body cells, acceleration of chemical processes, and the drying of wet hair, comprising:
    an applicator comprising:
        a plurality of diodes for emitting light;
        a coil for producing an electromagnetic field;
        a heating element;
        a fan for producing an air flow; and
        a control and power unit for activating the diodes, coil, heating element, and fan;
    wherein the applicator is substantially bowl-shaped, having a closed vertex at a first end, a substantially circular opening at a second end defining a plane, and a longitudinal axis extending between said first and second ends and being perpendicular to said plane of said opening.

8. The device according to claim 7, wherein:
    the coil is a substantially flat spiral winding located proximate to the vertex and in a plane perpendicular to the longitudinal axis; and
    said plurality of diodes are arranged around the applicator's interior.

9. A device for stimulation of body cells, acceleration of chemical processes, and the drying of wet hair, comprising:
    an applicator comprising:
        a plurality of diodes for emitting light;
        a coil for producing an electromagnetic field;
        a heating element;
        a fan for producing an air flow, and
        a control and power unit for activating said diodes, said coil, said heating element, and said fan;
        said applicator further comprising:
            a substantially cylindrical body open at a first end and closed at a second end; and
            a handle affixed to the body near the second end and substantially radial to the body,
            whereby the applicator is susceptible of deployment by hand.

* * * * *

Disclaimer

6,450,941 B1 — Eric Larsen, Schaffhausen (CH). DEVICE FOR THE STIMULATION OF BODY CELLS THROUGH ELECTROMAGNETIC RADIATION. Patent dated September 17, 2002, Disclaimer filed January 27, 2005, by the Inventor.

This patent is subject to a terminal disclaimer.

*(Official Gazette June 14, 2005)*